United States Patent [19]
Ulmer et al.

[11] Patent Number: 6,025,501
[45] Date of Patent: *Feb. 15, 2000

[54] DERIVATIZED POLYMERS OF α-OLEFIN-MALEIC ANHYDRIDE ALKYL HALF-ESTER OR FULL ACID

[75] Inventors: Herbert W. Ulmer, Hoboken; Timothy Gillece, Pompton Plains; John A. Katirgis, West Caldwell; Linda C. Foltis, Nutley; April Blaine, Highland Lakes, all of N.J.

[73] Assignee: ISP Investments Inc., Wilmington, Del.

[*] Notice: This patent is subject to a terminal disclaimer.

[21] Appl. No.: 09/103,856

[22] Filed: Jun. 24, 1998

Related U.S. Application Data

[63] Continuation-in-part of application No. 08/845,669, Apr. 25, 1997, Pat. No. 5,869,695.

[30] Foreign Application Priority Data

Mar. 4, 1998 [WO] WIPO ............... PCT/US98/04240
Mar. 4, 1998 [WO] WIPO ............... PCT/US98/04240

[51] Int. Cl.$^7$ ............... C10M 133/16; C07D 207/40
[52] U.S. Cl. ............... 548/545; 548/546; 548/547
[58] Field of Search ............... 548/545, 546

[56] References Cited

U.S. PATENT DOCUMENTS 5,869,695   2/1999   Ulmer et al. ............... 548/545
5,886,194   3/1999   Ulmer et al. .

*Primary Examiner*—Floyd D. Higel
*Attorney, Agent, or Firm*—Walter Katz; William J. Davis; Marilyn J. Maue

[57] ABSTRACT

What is described herein are derivatized polymers of α-olefin-maleic anhydride alkyl half-ester or full acid, preferably the isobutylene compound, optionally with repeat units of maleamic acid and/or its corresponding maleimide therein. These polymers are useful as fixatives in personal care products, such as hair spray compositions, particularly as one-phase, low VOC formulations in pump and aerosol systems, and in anhydrous, alcoholic, aqueous-alcoholic and in high hydrocarbon tolerant solvent formulations. In use, these hair spray compositions dry down to form clear, continuous and defectless films.

6 Claims, No Drawings

DERIVATIZED POLYMERS OF α-OLEFIN-MALEIC ANHYDRIDE ALKYL HALF-ESTER OR FULL ACID

CROSS REFERENCE TO RELATED COPENDING APPLICATIONS

This application is a continuation-in-part of Ser. No. 08/845,669, filed Apr. 25, 1997, now U.S. Pat. No. 5,869,695, and assigned to the same assignee.

BACKGROUND OF THE INVENTION

1. Field of the Invention

This invention relates to polymers of maleic anhydride, and, more particularly, to polymers of α-olefin-maleic anhydride alkyl half-ester or full acid, optionally with repeat units of maleamic acid and/or its maleimide, and to hair spray compositions which include these polymers as fixatives.

2. Description mof the Prior Art

Hair spray compositions usually contain film-fomrmming polymers as fixatives in a suitable delivery system. Recent governmental legislation, however, has required that hair spray compositions contain only 80m% or less VOC materials therein, preferably 55m% VOC. Accordingly, there has been a considerable effort in the cosmetic industry to provide useful polymers in hair spray formulations which meet the requisite VOC standard. Particularly sought-after are polymers which can provide one-phase compositions which dry down to form continuous, clear and defectless films.

Accordingly, an object of this invention is to provide new and improved polymers for use as fixative in personal care products, such as hair spray compositions, preferably in low VOC systems.

This and other objects and features of the invention will be made apparent from the following description of the invention.

SUMMARY OF THE INVENTION

What is described herein are polymers of α-olefin-maleic anhydride alkyl half-ester or full acid, optionally with repeat units of maleamic acid and/or its corresponding maleimide therein. These polymers are particularly useful as fixatives in hair spray compositions, particularly as one-phase, 55–80% VOC formulations in both pump and aerosol applications, in anhydrous or aqueous-alcoholic formulations, and in high hydrocarbon tolerant formulations. In use, these compositions dry down to form continuous, clear and defectless films.

DETAILED DESCRIPTION OF THE INVENTION

The polymers of the inventon contain repeat units of an α-olefin-maleic anhydride alkyl half-ester or full acid, optionally with repeat units maleamic acid and/or maleimide. Their general formula is given below:

FORMULA I

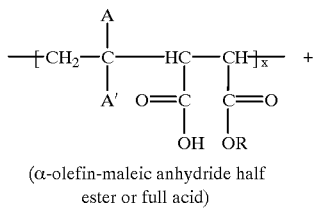

(α-olefin-maleic anhydride half ester or full acid)

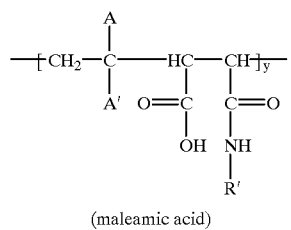

(maleamic acid)

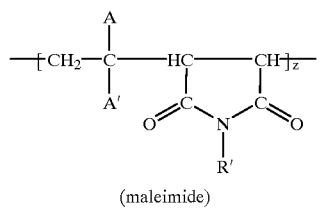

(maleimide)

where A and A' are independently H or $C_1$–$C_4$ alkyl;

R is H or $C_1$–$C_4$ alkyl and R' is an ma-unsubstituted primary amine; and x is 0.01–1; y is 0–0.95; and z is 0–0.99.

The derivatized polymers of the invention are made by reacting an a-olefin-maleic anhydride copolymer or α-olefin-maleic anhydride alkyl half-ester copolymer, having the formula:

FORMULA II

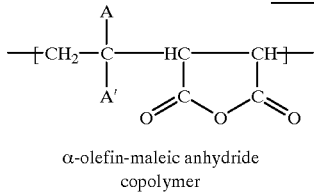

α-olefin-maleic anhydride copolymer

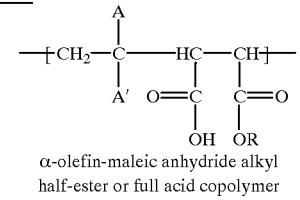

α-olefin-maleic anhydride alkyl half-ester or full acid copolymer in an aqueous, alcohol or aqueous-alcoholic solution, ROH, where R is as defined above, with an α-unsubstituted primary amine, $RNH_2$, such as n-hexylamine, n-octylamine or 2-ethylhexylamine. Ammonia, or a silated primary amine, fluorinated primary amine, halogenated primary amine, unsaturated amine, cyanoamine, alcohol amines and amphoteric amines, also may be used. The reaction is carried out at a reaction temperature of about 80–150° C., preferably about 100–130° C., for about 1–25 hours, preferably 2–10 hours.

In one embodiment of the invention, a polymer having no amide repeat unit, i.e. all amide has been converted to the cyclic imide form, can be obtained by carrying out the process at 115° C. for 5 hours or longer. The resultant polymer thus includes only half-ester and cyclic imide repeat units therein.

Higher reaction temperatures and longer reaction times enhance the conversion of amide into the corresponding cyclic imide repeating unit by loss of a water molecule.

The α-olefin-maleic anhydride or α-olefin-maleic anhydride alkyl half-ester copolymers used as starting materials in the process of the invention are made by a suspension polymerization method in a hydrocarbon solvent. In this method, the suspending agent and a free radical polymerization initiator are charged to a reactor and purged with nitrogen gas. Then the reactor is heated to 60° C. and a predetermined amount of molten maleic anhydride is introduced into the reactor vessel. Then the reactor is heated to 80° C and isobutylene is fed in continuously over a predetermined amount of time. The resultant feed rate is based on the efficiency of removal of heat from the system which is evolved during the polymerization reaction. Upon completion of the reaction, a white suspension of the polymer in the solvent is obtained which can be dried to provide a free-flowing, white powder of the desired copolymer.

Alternatively, the suspension can be pumped into a reactor and sparged with heated ethanol or water to remove the lower boiling hydrocarbon solvent and effect conversion of the anhydride polymer to its corresponding ethyl half-ester or diacid derivative.

Preferably the suspension polymerization is carried out under these conditions:

(a) the reactant solids are maintained at about 20 to 50%, preferably about 30%;

(b) the suspending agent is a hydrocarbon soluble resin, preferably containing maleic anhydride, e.g. p(octadecylvinylether-co-maleic anhydride) or p(octadecylene-co-maleic anhydride);

(c) the suspending agent is present in an amount of about 0.25 to 3 wt. % solids;

(d) the isobutylene reactant is fed into molten maleic anhydride over a period of about 2 to 6 hours, most preferably about 4 hours;

(e) the initiator is an azo or peroxide initiator, with a half-life of at least 10 hours at a reaction temperature between about 60° and 90° C., preferably, a peroxide initiator;

(f) the reaction temperature is at least 80mOC; and (g) the hydrocarbon solvent is pentane or hexane.

Alternatively, the starting polymers of FORMULA I may be made by precipitation polymerization in a solvent such as isopropyl acetate.

HAIR SPRAY COMPOSITIONS

During drying, hair spray compositions containing polymers of the invention derivatized with long chain amines form films which go through a gel-like state upon further drying. The resultant film is a continuous, clear, defectless film.

The invention will now be illustrated by the following examples.

1. Preparation of Starting Materials

EXAMPLE 1

To a 2-liter, high pressure reactor was added: 98.06 g maleic anhydride monomer, 2.94 g decanoylperoxide initiator, 3.85 g octadecylvinylether as suspending agent and 240 g of pentane as solvent. Then the reactor was sealed and purged 3 times with nitrogen gas. The reactor was heated to 80° C. over a 30 minute period. Upon reaching 80° C., 141,64 ml of isobutylene monomer was fed into the reactor over a 4-hour period. The reaction was continued for another 1 hour at 80° C. and then cooled and discharged. The resultant product was a finely divided, off-white slurry of poly(isobutylene-maleic anhydride) copolymer in pentane.

2. preparation of Copolymers of Formula I

EXAMPLE 2

Into a high pressure reactor was added: 75.4 g (0.490 mole) P(isobutylene-MAn) powder, 19.8 g octadecylamine (0.0735 mole) and 222.1 g ethanol. The reaction mixture was then purged with $N_2$ gas and the temperature was raised to 50° C. and held there for 1 hour. Then the temperature was increased to 75° C., held for 2 hours, and thereafter to 100° C. for 3 hours. Upon cooling the resultant product had a slightly green color and a slight haze. The dried polymer had an acid of 225 mg KOH/g polymer and contained about 2 wt. % free amine.

EXAMPLE 3

Copolymer of Fmormmula I

In a high pressure reactor was added: 60.86 g (0.395 mole) p(isobutylene-MAn) powder, 15.90 g (0.0590 mole) n-octadecylamine, 4.32 g (0.0590 mole) n-butylamine, and 270.3 g ethanol.

The resultant reaction slurry was stirred, sealed and purged with $N_2$ gas. The temperature was raised to and kept at 75° C. for 2 hours and then raised to and kept at 100° C. for 2 hours. Upon cooling, the reaction product was a clear slightly yellow solution. The resultant polymer had an Acid No. of 202 mg KOH/g polymer and 0.142 meq. free amine/g of product.

EXAMPLE 4

In a high pressure reactor was added: 65 g (0.422 mole) p(isobutylene-MAn) powder, 11.4 g (0.0423 mole) octadecylamine, 10.9 g (0.0843 mole) octylamine, and 204 g ethanol.

The resultant slurry was stirred, sealed and purged with $N_2$ gas. The temperature was raised to and kept at 75° C. for 2 hours and then raised to and kept at 100° C. for 5 hours. Upon cooling, the reaction product was a clear slight yellow solution. The resultant polymer had an Acid No. of 198 mg KOH/g polymer and 0.146 meq. free amine/g product.

EXAMPLE 5

To a 2-liter, high pressure reactor was added: 60.0 g (0.390 mole) p(isobutylene-maleic anhydride), 8.54 g (0.117 mole) n-butylamine, 10.82 g dodecylamine, 15.73 g (0.0584 mole) octadecylamine and 285 g ethanol. The reactor was purged with $N_2$ gas. The reactor was heated to 75° C. and held for 2 hours and then heated to 100° C. and held for 5 hours. The resultant material possessed an acid number of 146 mg KOH/g polymer.

EXAMPLE 6

To a 2-liter, high pressure reactor was added: 66.1 g (0.429 mole) p(isobutylene-maleic anhydride), 10.96 g (0.150 mole) n-butylamine, 11.90 g (0.0642 mole) dodecylamine, 5.77 g (0.0214 mole) octadecylamine and 285 g ethanol. The reactor was purged with $N_2$ gas. The reactor was heated to 75° C. and held for 2 hours and then heated to 100° C. and held for 5 hours. The resultant material possessed an acid number of 160 mg KOH/g polymer.

EXAMPLE 7

To a 2-liter, high pressure reactor was added: 64.7 g (0.420 mole) p(isobutylene-maleic anhydride), 8.14 g (0.0630 mole) 2-ethylhaxylamine and 16.97 g (0.0630 mole) octadecylamine and 200 g ethanol. The. reactor was purged with $N_2$ gas. The reactor was heated to 75° C and held for 2 hours and then heated to 100° C. and held for 5 hours. The resultant material possessed an acid number of 205 mg KOH/g polymer.

EXAMPLE 8

To a 2-liter, high pressure reactor was added: 73.4 g (0.477 mole) p(isobutylene-maleic anhydride), 10.45 g (0.143 mole) n-butylamine and 12.83 g (0.0476 mole) octadecylamine and 171 g ethanol. The reactor was purged with $N_2$ gas. The reactor was heated to 75° C. and held for 2 hours and then heated to 100° C. and held for 5 hours. The resultant material possessed an acid number of 195 mg KOH/g polymer.

EXAMPLE 9

To a 2-liter, high pressure reactor was added: 66.0 g p(isobutylene-maleic anhydride and 198 g ethanol. The reactor was purged with $N_2$ gas. The reactor was heated to 130° C. and held for 8 hours. The resultant material possessed an acid number of 265 mg KOH/g polymer.

EXAMPLE 10

To a 2-liter, high pressure reactor was added: 66.0 g (0.429 mole) p(isobutylene-maleic anhydride, 5.80 g (0.129 mole) ethylamine, 9.40 g (0.129 mole) n-butylamine and 198 g ethanol. The reactor was purged with $N_2$ gas. The reactor was heated to 100° C. and held for 3 hours and then the reactor was heated to 130° C. and held for 5 hours. The resultant material possessed an acid number of 120 mg KOH/g polymer.

EXAMPLE 11

Into a high pressure reactor was added: 22.8 g (0.148 mole) p(ImB-MmMn), 3.33 g ethylamine (0.0517 mole) (70%), 2.96 g water and 45.62 g ethanol. The reaction was purged with $N_2$ gas and the temperature raised to 100° C. over 1 hour. Upon reaching 100° C., 5.44 g (0.0891 mole) ethanolamine dissolved in 19.85 g water was added to the reaction mixture. The reaction was held at 100° C. for 1 hour and then raised to 130° C. over 1 hour and held for an additional 8 hours. Cooling provided a clear yellow solution. The dried polymer had an acid number of only about 25 mg KOH/g polymer, indicating substantially all maleimide repeat units in the polymer.

EXAMPLE 12

Into a high pressure reactor was added: 154.0 g (1.00 mole) p(IB-MAn), 9.02 g ((0.140 mole) ethylamine (70%), 10.97 g (0.150 mole) butylamine and 316 g ethanol. The reaction was purged with $N_2$ gas and the temperature raised to 130° C. over 2 hours and held for 3 hours. The reaction mixture was cooled to which was added 36.65 g (0.600 mole) of ethanolamine dissolved in 176 g of water. The reactor was gradually reheated to 130° C. over 3 hours and held for 8 hours. A clear yellow solution provided a polymer having an acid number of about 65 mg KOH/g polymer.

EXAMPLE 13

Hair/Spray/Composition Containing the Polymers of Examples 1–10

Low VOC hair spray compositions containing 5% by weight of each of the polymers of Examples 1–10 are prepared in ethanol and, optionally a hydrocarbon system.

The polymers are neutralized with organic amines.

Typical formulations thus contained 65% ethanol, 15% hydrocarbon, 15% water and S% polymer (80% VOC); or 55% ethanol, 40% water and 5% polymer (50% VOC). The observed high humidity curl retentions for these systems were excellent.

EXAMPLE 13A

The polymers of the invention is formulated into a hydroalcoholic pump hair spray system containing as little as 3.5% water and a maximum of 91% water (VOC 4–92%).

| Formula I | |
|---|---|
| SD Alcohol 40B 200, Anhydrous | 87.50% |
| Deionized Water | 0.00 |
| Imidized IB/MA Copolymer | 12.50 |
| (40% solids, 27% $H_2O$, 33% EtOH) | |
| Formula II | |
| SD Alcohol 40B 200, Anhydrous | 0.00% |
| Deionized Water | 87.50 |
| Imidized IB/MA Copolymer | 12.50 |
| (40% solids, 27% $H_2O$, 33% EtOH) | |

EXAMPLE 13B

The polymers of the invention is formulated into. a single phase hydroalcoholic aerosol hair spray system having a VOC content of 35% to 95%, with dimethyl ether as the propellant.

| Formula III | |
|---|---|
| SD Alcohol 40B 200, Anhydrous | 52.50% |
| Deionized Water | 0.00 |
| Imidized IB/MA copolymer | 12.50 |
| (40% solids, 27% $H_2O$, 33% EtOH) | |
| Dimethyl Ether | 35.00 |
| Resin solids 5% | |

-continued

| Formula IV | |
|---|---|
| SD Alcohol 40B 200, Anhydrous | 0.00% |
| Deionized Water | 52.50 |
| Imidized IB/MA Copolymer | 12.50 |
| (40% solids, 27% H$_2$O, 33% EtOH) | |
| Dimethyl Ether | 35.00 |
| Resin solids 5% | |

| Formula V | |
|---|---|
| SD Alcohol 40B 200, Anhydrous | 15.88% |
| Deionized Water | 35.92 |
| Imidized IB/MA Copolymer | 12.50 |
| (40% solids, 27% H$_2$O, 33% EtOH) | |
| Ammonium Hydroxide | 0.30 |
| MEA Borate (and) MIPA Borate | 0.40 |
| Dimethyl Ether | 35.00 |
| Resin solids 5% | |
| (Corrosion resistant in | |
| unlined tinplate cans) | |

| Formula VI | |
|---|---|
| SD Alcohol 40B 200, Anhydrous | 15.88% |
| Deionized Water | 35.92 |
| Imidized IB/MA Copolymer | 12.50 |
| (40% solids, 27% H$_2$O, 33% EtOH) | |
| Ammonium Hydroxide | 0.15 |
| Dimethyl Oxazolidine | 0.15 |
| MEA (and) MIPA Borate | 0.40 |
| Dimethyl Ether | 35.00 |
| Resin solids 5% | |

The Formulas I–VI above also provide stiff feel on the hair at 5% resin solids comparable to an 80% VOC maximum hold, obtained with conventional retail hair sprays. In addition, advantageous humidity resistance (95% curl retention after exposure to 90% relative humidity, 80° F. for 4 hours) is achieved in these 55% VOC hair sprays.

While the invention has been described with particular reference to certain embodiments thereof, it will be understood that changes and modifications may be made which are within the skill of the art. Accordingly, it is intended to be bound only by the following claims, in which:

What is claimed is:

1. A polymer which contains repeat units of an α-olefin-maleic anhydride alkyl half-ester or fill acid, maleamic acid and maleimide units, having the formula:

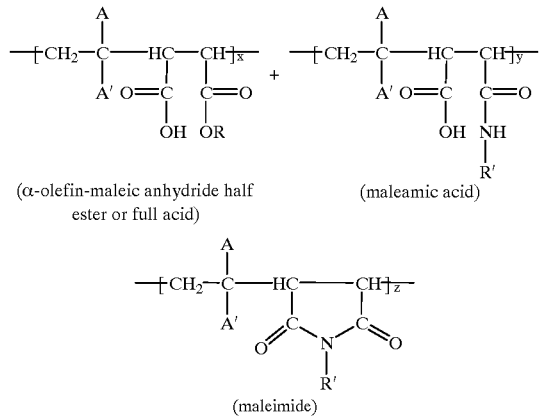

(α-olefin-maleic anhydride half ester or full acid) (maleamic acid)

(maleimide)

where A is independently H or $C_1$–$C_4$ alkyl;

R is H or $C_1$–$C_4$ alkyl, and R' is an α-unsubstituted primary amine; and x is 0.01–1; y is 0–0.95; and 0–0.99 is 0.99.

2. A polymer according to claim 1 wherein R is ethyl.

3. A polymer according to claim 1 wherein A and A'=H.

4. A polymer according to claim 1 wherein A=H and A'=CH$_3$.

5. A polymer according to claim 1 wherein A anmd A'=CH$_3$.

6. A composition which includes the polymer of claim 1.

* * * * *